(12) United States Patent
Pickles et al.

(10) Patent No.: US 8,491,765 B2
(45) Date of Patent: *Jul. 23, 2013

(54) DIAMOND MICROELECTRODES

(75) Inventors: Charles Simon James Pickles, Twickenham (GB); Clive Edward Hall, Nijmegen (NL); Li Jiang, Cambridge (GB); Neil Perkins, Reading (GB); Richard Antonius Kleijhorst, Cuijk (NL)

(73) Assignee: Element Six Limited, Ballasalla (GB)

(\*) Notice: Subject to any disclaimer, the term of this patent is extended or adjusted under 35 U.S.C. 154(b) by 0 days.

This patent is subject to a terminal disclaimer.

(21) Appl. No.: 13/190,090

(22) Filed: Jul. 25, 2011

(65) Prior Publication Data

US 2012/0037505 A1  Feb. 16, 2012

Related U.S. Application Data

(60) Division of application No. 10/567,028, filed as application No. PCT/IB2004/002404 on Jul. 27, 2004, now Pat. No. 8,177,949, which is a continuation-in-part of application No. 10/637,500, filed on Aug. 11, 2003.

(30) Foreign Application Priority Data

Aug. 4, 2003 (GB) .................................. 0318215.1

(51) Int. Cl.
*G01N 27/26* (2006.01)
*G01N 27/403* (2006.01)

(52) U.S. Cl.
USPC ........... 204/400; 204/409; 204/433; 204/412; 204/280; 204/294

(58) Field of Classification Search
USPC ................ 204/400, 415, 416, 418, 294, 409, 204/433, 412, 280
See application file for complete search history.

(56) References Cited

U.S. PATENT DOCUMENTS

| 5,089,802 A | 2/1992 | Yamazaki |
| 5,173,761 A * | 12/1992 | Dreifus et al. ................... 257/22 |
| 5,300,188 A | 4/1994 | Tessmer et al. |
| 5,405,618 A | 4/1995 | Buttery et al. |
| 5,603,820 A | 2/1997 | Malinski et al. |

(Continued)

FOREIGN PATENT DOCUMENTS

| EP | 1 156 136 | 11/2001 |
| JP | 4312982 A | 11/1992 |

(Continued)

OTHER PUBLICATIONS

Madore et al. (Proceedings of the Symposium on Microfabricated Systems and MEMS, 2000).*

Madore C., et al., "Detection of Trace Silver and Copper at an Array of Boron-Doped Diamond Microdisk Electrodes", Proceedings of the Symposium on Microfabricated Systems and MEMS, vol. 2000-19, pp. 159-168, 2000.

(Continued)

*Primary Examiner* — J. Christopher Ball
*Assistant Examiner* — Jennifer Dieterle
(74) *Attorney, Agent, or Firm* — Oblon, Spivak, McClelland, Maier & Neustadt, L.L.P.

(57) ABSTRACT

A microlectrode comprising a diamond layer formed from electrically non-conducting diamond and containing one or more pins or projections of electrically conducting diamond extending at least partially through the layer of non-conducting diamond presenting areas of electrically conducting diamond.

17 Claims, 2 Drawing Sheets

U.S. PATENT DOCUMENTS

| | | | |
|---|---|---|---|
| 5,711,861 A * | 1/1998 | Ward et al. | 600/347 |
| 5,795,453 A * | 8/1998 | Gilmartin | 204/403.03 |
| 5,844,252 A * | 12/1998 | Shiomi et al. | 257/10 |
| 6,599,841 B2 | 7/2003 | Komada | |
| 8,177,949 B2 * | 5/2012 | Pickles et al. | 204/294 |
| 2002/0120296 A1 * | 8/2002 | Mech et al. | 607/2 |

FOREIGN PATENT DOCUMENTS

| | | |
|---|---|---|
| JP | 5018935 A | 1/1993 |
| JP | 8240555 A | 9/1996 |
| JP | 2002286692 A | 10/2002 |
| JP | 2003121410 A | 4/2003 |
| JP | 2005005659 A | 1/2005 |
| WO | WO 2004/005585 A1 | 1/2004 |

OTHER PUBLICATIONS

Fujishima Akira et al., "New Directions in Structuring and Electrochemical Applications of Boron-Doped Diamond Thin Films", Diamond and Related Materials, vol. 10, No. 9-10, pp. 1799-1803, 2001.

Soh K. L. et al., "CVD Diamond Anisotropic Film as Electrode for Electrochemical Sensing", Sensors and Actuators B, vol. 91, No. 1-3, pp. 39-45, 2003.

Lisa Y.S. Pang, et al. "High Temperature Polycrystalline Diamond Metal-Insulator-Semiconductor Field-Effect-Transistor", Diamond and Related Materials, vol. 6, Jan. 1, 1997, pp. 333-338.

* cited by examiner

DIAMOND MICROELECTRODES

CROSS REFERENCE TO RELATED APPLICATION

This application is a Continuation Application of U.S. application Ser. No. 10/567,028, filed Oct. 11, 2006, the entire contents of which are incorporated herein by reference. U.S. application Ser. No. 10/567,028 is a National Stage of PCT/IB2004/002404, filed Jul. 27, 2004, which is a nonprovisional of application Ser. No. 10/637,500, filed Aug. 11, 2003 and claims benefit of priority under 35 U.S.C. 119 of United Kingdom Application No. 0318215.1, filed Aug. 4, 2003.

BACKGROUND OF THE INVENTION

This invention relates to diamond microelectrodes.

Electrochemistry utilises the relationship between current and voltage measured on immersed electrodes to characterise the solution in which the electrode is immersed. Dependent on the application, one of the current or voltage may be fixed and the other parameter allowed to vary, for example as the solution varies. Alternatively the solution may be essentially fixed, and one of the current or voltage may be swept across a range of values and the response in the other parameter recorded in the form of a time/current plot or voltammogramme.

Electrochemical measurements can be qualitative or comparative, or they may be quantitative. Quantitative measurements generally require that the system is amenable to mathematical modelling, and in both cases it is desirable that the signal to noise in the system is maximised and that as much information as possible is extracted from the system (see Feeney et al, Electroanalysis 200, 12 no. 9). Both of these objectives can best be achieved by using small electrodes, i.e. microelectrodes, such that the configuration approximates to a semi-spherical or three dimensional diffusion model rather than either a linear or two dimensional diffusional model.

The use of such microelectrodes is well known in the art, and became an active field of research in the late 1970's. Subsequent general development of electronics has provided the tools required to utilise such electrodes efficiently. Typical benefits realised include increased temporal resolution, increased current density, decreased sensitivity to solution resistance, and steady state diffusion profiles.

From the point of view of the analysis, the simplest microelectrode is a hemisphere, matching the mathematical geometry of constant concentration surfaces further out into the fluid. However, for a planar disc at large values of $D_o t/r_o^2$ (where $D_o$ is the diffusion coefficient of the species being electrolyzed, t is the time after applying the voltage and $r_o$ is the radius of the electrode), a hemispherical diffusion layer can typically be envisioned over the disc and the geometry is still amenable to analysis. For arrays of electrodes in a static system, the behaviour of the system depends on the electrode spacing. For short times, or large electrode spacings, the electrodes behave independently and the total output of an array electrically connected in parallel is the sum of the outputs of the individual electrodes. For long times, or closely spaced electrodes, the individual diffusion profiles overlap and in the extreme the system behaves like a single electrode with a total area of that of the array (sum of individual electrode areas and the intervening insulator). In flowing systems, the characteristic time remains generally short, dependent on the flow rate.

Typically, in order to fabricate such microelectrodes, a conductive electrode material such as a metal is coated with a non-conducting layer which is then perforated with one or more apertures to form the microelectrodes which will come into contact with the solution. More recently, boron doped CVD diamond has become established as an electrode material, and fabrication of microelectrodes onto a boron doped diamond layer has been reported. Typically such electrodes are a few microns in diameter, fabricated by applying a layer of $Si_3N_4$ or similar non-conductive material to the surface of the diamond and subsequently etching apertures into it to expose the diamond underneath (e.g. P Rychen et al., Electrochemical Society Proceedings Vol. 2001-23 pp 97-107).

SUMMARY OF THE INVENTION

According to the present invention, a microelectrode comprises a diamond layer formed from electrically non-conducting diamond and containing one or more pins or projections of electrically conducting diamond extending at least partially through the layer of non-conducting diamond and presenting areas of electrically conducting diamond. Preferably the pins or projections extend to a surface of the layer of electrically non-conducting diamond presenting areas of electrically conducting diamond co-planar with that surface (the "analysis surface").

The areas of electrically conducting diamond will preferably be co-planar with the analysis surface. However, the areas may be recessed relative to the analysis surface creating a well or reservoir for electrochemical sensing (bio-) chemicals such as polymers containing antigens, or semi-permeable membranes such as Nafion. These additives to the reservoir or wells will generally present a surface co-planar with the analysis surface.

The areas of electrically conducting diamond in the analysis surface preferably present a round profile on the analysis surface, although other shapes may be used dependent on the application and method of fabrication.

The areas of electrically conducting diamond are in electrical connection to one or other surfaces of the diamond layer through which they can be connected to an external circuit. This other surface or surfaces will be referred to as "the contact surface".

In one variant of the invention, the areas of electrically conducting diamond may be internally electrically connected within the diamond layer into one or more groups of electrodes. In another variant, the areas of electrically conducting diamond may be externally connected into one or more groups of electrodes.

The invention provides, according to another aspect, an electrochemical cell which includes a microelectrode of the type described above.

The conductive regions of the diamond may be generated by any method known in the art, but are preferably produced by the addition of dopant elements. Doping can be achieved by implantation, but is preferably achieved by incorporation of the dopant element during synthesis of the diamond, e.g. during synthesis of the diamond by chemical vapour deposition (CVD).

External connection and interconnection of the electrodes can be achieved by a variety of means. For example the contact surface of the diamond could be provided with a series of contact pads onto which individual wire bonds are made, or a ball-grid array substrate is soldered, and the choice of how to group electrodes made in external circuitry. Alternatively, the contact surface of the diamond could be coated with one or more layers of conductive material, optionally in combination with one or more non-conductive layers, to provide 'on board' interconnection. A simple form of this 'interconnection layer' may comprise a uniform or patterned metallization layer on the contact surface of the diamond layer. Other conducting layers may include a layer of conductive diamond such as boron-doped diamond, a metal, doped silicon or any other electrically conducting material.

The area or areas of electrically conductive diamond in the analysis surface act as the electrochemical electrode surface or surfaces and come into contact with the fluid under analysis. The fluid is generally a liquid, but may also be a gas. The whole electrode structure, comprising for example of diamond layer with co-planar conductive electrodes, interconnection layer where used and any additional bonding wires, can be used as is or the structure can be fitted into an electrode holder, such as a Teflon tube, or by some other means packaged to protect the structures behind the analysis surface.

The diamond microelectrode structure of the invention offers the following advantages over prior art.

1. The electrode structure, in a preferred form, is truly planar, enabling simple, typically algebraic, modelling of a planar structure to represent accurately the geometry of the system. In systems using an insulating layer patterned on to a conductive layer, as the electrode dimensions are reduced the thickness of the insulating layer generates an increasing perturbation to the simple model.
2. The dimensions of the conducting electrode areas are not determined by the need to keep the diameter significantly larger than the thickness of the insulating layer, enabling electrode dimensions to be optimised for the particular application.
3. The entire analysis surface (conducting regions and non-conducting areas), in a preferred form, is diamond thus exhibiting similar behaviour and a high degree of stability under aggressive environmental conditions. In particular the electrode is extremely robust to aggressive chemistry, and to abrasion which may occur in some applications, ensuring that the geometry of the analysis surface remains stable in use, and that the life of the device is extended. Diamond is generally accepted to have extremely high chemical inertness, and extremely high resistance to abrasion.
4. In systems with flow, the flow across the planar analysis surface is laminar, further simplifying analysis if measurements are taken during flow, ensuring that trapped boundary layers do not occur, and further reducing abrasion in abrasive fluids.
5. Surface properties of the analysis surface such as wettability and adherence of the fluid under analysis or any of its components is essentially uniform across the analysis surface.
6. Cleaning of the planar analysis surface is much simpler than for surfaces with delicate or fine non-planar structures.
7. There is no risk of leakage or electrolyte creep between the conducting regions and the non-conducting regions of the analysis surface.
8. When used in conjunction with electrochemical mediating (bio-) chemicals, with the surface of the conducting diamond recessed back to provide a well for these chemicals to fill, these wells are dimensionally stable and can be easily filled. In addition, the excess of the mediating (bio-) chemical can be simply removed mechanically by means of a blade, a scraper or by mechanical abrasion as there will be no damage to the diamond part of the analysis surface.
9. The diamond electrodes are inert and can be used at high over voltages. In addition the diamond electrodes can have the polarity reversed, or be treated by using aggressive chemical etches for cleaning purposes or to remove exhausted electrochemical mediating (bio-) chemicals.

DESCRIPTION OF EMBODIMENTS

Figure 1:
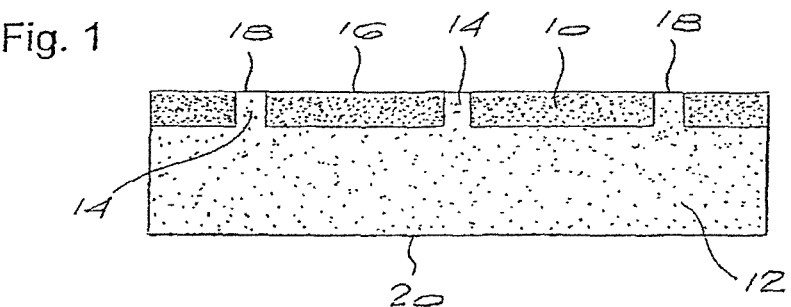
FIGS. 1 to 4 and 6 illustrate sectional side views of five different embodiments of the invention.

The diamond layer forming the analysis surface may be single crystal or polycrystalline in nature and will usually be synthetic, although it is possible to fabricate the device from natural diamond. Synthetic diamond includes high pressure high temperature (HPHT) diamond or chemical vapour deposition (CVD) diamond. The co-planar surface will generally be smooth and preferably polished to a surface roughness of less than 100 nm Ra, although the precise requirements on surface Ra are determined by the application and electrode geometry. Surface Ra values as low as 10 nm are easily achievable.

The conductive diamond in the layer forming the analysis surface can be fabricated by any method known to the art, but is preferably fabricated by doping during growth, and more preferably by doping with boron during growth. An alternative method of creating the conductive diamond regions is that of ion implantation. Alternative dopants include sulphur and phosphorus.

Generating the structure of the analysis surface can be achieved in a number of ways. The following are non-limiting examples:

a) An insulating diamond layer (natural or synthetic) may be polished flat on the rear face. A boron doped diamond layer is grown by HPHT or preferably by CVD on the rear face. The layer is polished into a thin flat layer from the front face, supported by the boron doped layer. Then suitable dopants are implanted in the pattern of the required electrode array, using for example B, such that the implanted dopant contacts the boron doped conducting layer on the rear face and extends to the front analysis face. Variants of this may use multiple energy implants, and implant moderators and/or removal of a surface layer after implant in order to bring the conducting implant to the very surface of the layer.

b) An insulating diamond layer (natural or synthetic) may be polished flat and parallel. This layer may then have features etched into one face, using for example plasma or chemical etching through a mask, chemical etching of implant damaged features, or laser etching, to generate etch features which when filled will become the electrodes. A boron doped diamond layer may then be grown by CVD methods onto this patterned surface, such that it fills the recesses processed into the surface. Polishing from the insulating face until the features are revealed provides a thin non-conducting layer with boron doped regions forming electrodes and a continuous boron doped layer to the rear connecting all the electrodes. Alternatively polishing from the front to remove the continuous boron doped layer would reveal the isolated regions of boron doped material. Further processing from the rear face could provide either a continuous contact layer or individual connections. For example, laser drilling down to the boron doped regions followed by filling with metallisation and individual wire bonding would suffice.

c) A preferred embodiment is as follows: A conducting diamond layer (natural or synthetic) may be polished flat and parallel. This layer may then have features etched into one face, using for example plasma or chemical etching through a mask, chemical etching of implant damaged features, or laser etching, to generate a series of pillars which will form the electrodes. A non-conducting diamond layer may then be grown by CVD methods onto this patterned surface, such that it fills the recesses surrounding the conducting diamond pillars. Polishing from this newly grown insulating face until the conducting pillars are revealed would provide a thin non-conducting layer with conducting regions forming electrodes and a continuous conducting layer to the rear connecting all the electrodes. Preferably both diamond layers will be grown by CVD, and the conducting layer will preferably be doped by boron during growth. Variations on this basic process, such as initial growth of the boron doped CVD layer onto a pre-shaped non-conducting layer, and multiple etch and growth steps, would provide for fabrication of electrodes connected for example in rows, in groups, or individually. Wells in the analysis layer may be provided by etching, using for example plasma or chemical etching through a mask, chemical etching of implant damaged features, or laser etching.

d) In the above examples, the initial diamond layer can be single crystal or polycrystalline. In general where the initial layer is single crystal the subsequently grown layers would also be single crystal, and likewise with a polycrystalline initial layer the subsequent layers would generally be polycrystalline. Single crystal devices may offer an advantage where the variation of boron uptake with growth sector is a consideration, affecting for example the conductivity, or where the geometry is so fine that it is difficult to form in polycrystalline diamond.

e) A particular method of fabrication in single crystal diamond makes use of the presence of controlled surface pits. Generation of surface pits by a combination of selection of the growth conditions and initial substrate surface preparation can generate a regular array of pits in a non-conducting diamond layer grown onto a single crystal substrate. Further overgrowth, either subsequently or in continuous sequential step, by a boron doped layer can infill these pits and produce a continuous connecting rear boron doped layer. Separation of the layer from the original single crystal substrate is then required, for example by sawing, polishing or preferential electrochemical etching along an interface formed from implant damage generated in the surface of the original substrate before use, followed by polishing to the final surface position and finish if necessary, would provide the structure required. Electrodes formed via pit features on a {100} surface generally form a square (edges along the <100> or <110>), or octagonal (from a combination of the two) outline where they intersect the final polished {100} surface.

The above methods of fabrication are not generally limited to a particular scale or particular dimensions, allowing these to be dictated by the application. Typical application requirements are electrodes with a radius in the range 1-100 μm, and most typically near 10 μm, with a ratio between the electrode separation and the electrode radius typically exceeding 5, more typically exceeding 10, and even more typically exceeding 20. Where polycrystalline diamond is used which is doped during growth it may be preferable for the electrode surface to comprise at least 10 grains or growth sectors and more preferably 30 grains or growth sectors to provide a statistically similar electrode at each position. In cases where the range of variation in boron (or other growth dopant) uptake and the resultant electrical conductivity found between different diamond growth sectors does not affect the result obtained at the electrode this can be ignored.

The interconnection layer or layers on the back of the layer presenting the analysis surface may also be boron doped diamond (although other dopants such as S and P may be used), made by any method known to the art but preferably by doping during CVD synthesis. An alternative is graphite, which may be grown or implanted, or generated in situ by laser or implantation damage, possibly modified by subsequent annealing. Other alternatives include metal which may be deposited and patterned using any standard technique such as vapour deposition, sputter deposition, electroplating, laser ablation etc.

Further embodiments of the invention will now be described with reference to the accompanying drawings. Referring first to FIG. 1, a microelectrode comprises a layer 10 of non-conducting diamond bonded to a layer 12 of conducting diamond. The conducting diamond layer 12 has projections, in the form of pins 14, which extend through the non-conducting diamond layer 10. The pins 14 terminate in the upper surface 16 of the layer 10 of non-conducting diamond and provide areas 18 of conducting diamond in this surface. This surface is the surface referred to as the "analysis surface". The surface 20 of the layer 12 of conducting diamond provides the contact surface.

Figure 2:
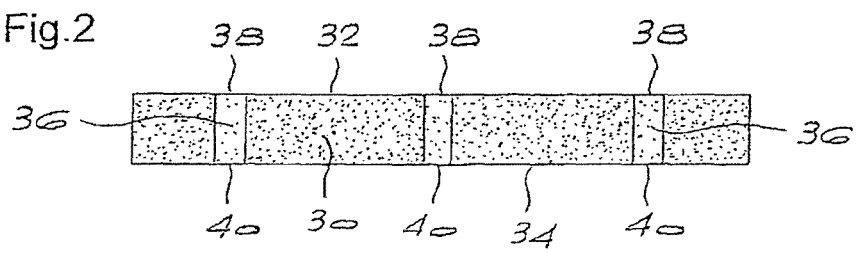

Referring to FIG. 2, a microelectrode comprises a layer 30 of non-conducting diamond having an upper surface 32 and a lower surface 34. Extending through the layer 30 is a plurality of spaced pins 36 of conducting diamond. The pins 36 terminate in the surfaces 32, 34 and provide areas 38, 40 of conducting diamond in these surfaces. Either surface 32 or 34 may be used as the analysis surface and the opposite surface is then the contact surface.

Figure 3:
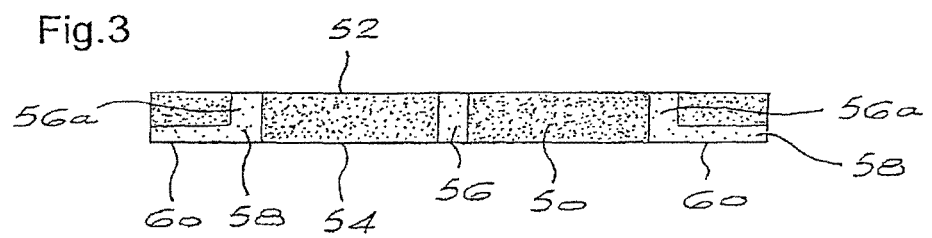

Referring to FIG. 3, a microelectrode comprises a layer 50 of non-conducting diamond having an upper surface 52 and a lower surface 54. Extending through the layer 50 from the upper surface to the lower surface are one (as shown) or more spaced pins 56 of electrically conducting diamond. Surrounding these pins is an electrode ring 56a which can have a variety of forms but is shown in this cross-section to have an L-shape in cross-section, presenting to the analysis face 52 as a thin ring, and providing contact surfaces on both the rear face 54 and the edges of the layer.

Figure 4:
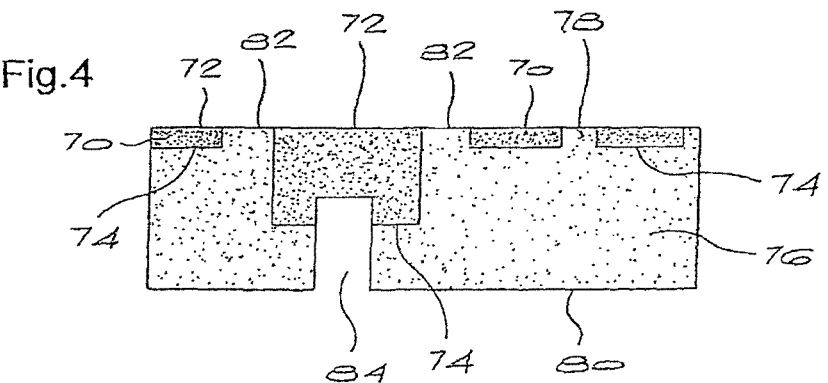

Referring to FIG. 4, a microelectrode comprises a layer 70 of non-conducting diamond having an upper surface 72 and a lower surface 74. Bonded to the layer 70 is a layer 76 of conducting diamond. This layer 76 has a plurality of spaced pins 78 extending through the layer 70 of non-conducting diamond presenting conducting areas 82 in the surface 72. An insulating gap 84 is cut through the layer 76 from the surface 80 and into the non-conducting layer 70, for example by laser cutting. This has the effect of isolating the pins into groups which are electrically connected together where a groove 84 does not separate them, with the groups isolated one from another by the selection of grooves 84 used. The insulating layer 70 may be of uniform thickness, or it may be advantageous to thicken this layer, as shown, in the locations where grooves 84 are to be made in order to provide sufficient thickness of material in which to terminate the cut 84.

Figure 5:
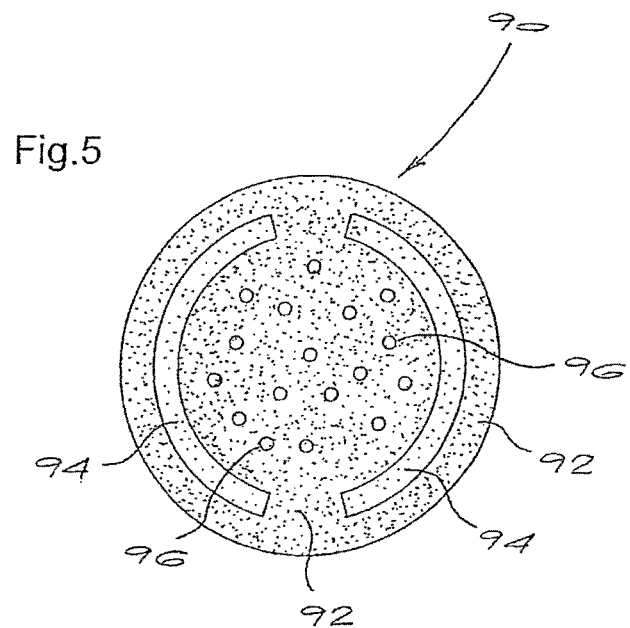
FIG. 5 illustrates a plan view of a sixth embodiment.

Yet a further embodiment is illustrated by FIG. 5. In electrochemical systems and processes it is generally required to have two types of electrode, and sometimes advantageous to have three or more. It is possible to provide within the diamond structure of the invention one or more type of electrode, differentiated by the voltage applied or by the use made of it by external circuitry, or by the electrochemical sensing chemicals used in conjunction with the electrode where these are used, or by concentration or type of dopant, or merely by the geometry or size of the electrode. A particular example is the use of three electrodes, the 'reference electrode' and the +ve and −ve electrodes which are generally termed the Working electrodes', and one of which may be called the 'counter-electrode' depending on the electrochemistry in use. Referring to FIG. 5, the top analysis surface 90 of a microelectrode is shown. This surface is part of a layer of non-conducting diamond 92. Located in this layer 92 are two crescent-shaped bodies 94 of conducting diamond and a plurality of spaced pins 96 located within the area enclosed by the crescent bodies 94 and presenting conducting areas in the analysis surface. In this particular case, one of the crescent shaped bodies forms the reference electrode, the other forms the counter electrode, and the multiple pins form the other working electrode. One method of making the structure in FIG. 5 is to first synthesise an electrically conducting boron doped diamond layer, fabricating on one surface of this layer the electrode structures required by etching the material away in between, for example by using laser etching, then growing the insulating diamond layer on top, and subsequently polishing back to planarise the surface and expose the boron doped electrodes in order to create the analysis surface. This method alone would however leave the various electrode types interconnected by the continuous layer of boron doped material forming the rear face. The method illustrated in FIG. 4 could then be used, cutting laser grooves through the rear boron doped layer into the back of the insulating diamond layer in a geometry which provides electrical isolation between the different electrodes as required.

Figure 6:
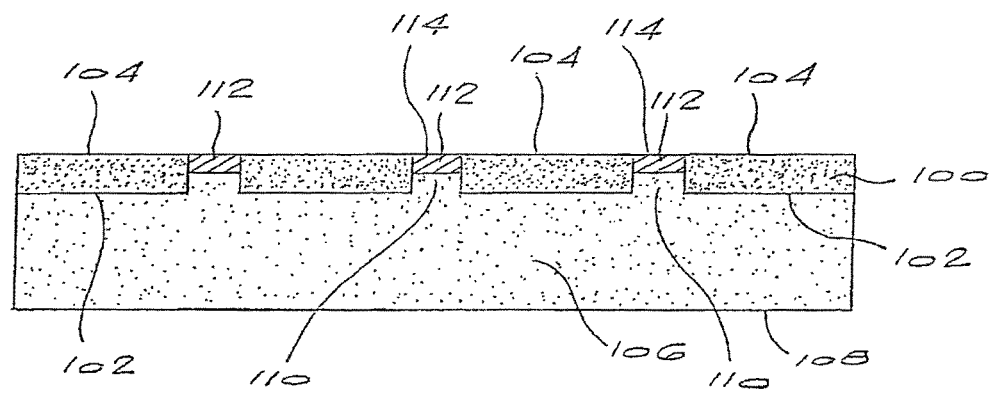

Referring to FIG. 6, a microelectrode comprises a layer 100 of non-conducting diamond having a lower surface 102 and an upper surface 104. Bonded to the lower surface 102 is a layer 106 of conducting diamond. The layer 106 of conducting diamond has a lower surface 108 and a plurality of spaced projections or pins 110 extending into the layer 100 of non-conducting diamond. The pins 110 do not extend to the surface 104 and create wells or recesses 112 in layer 100. In use, this microelectrode will be used in combination with electrochemical sensing chemicals or semi-permeable membranes which fill the wells or recesses 112. These chemicals or membranes fill the recesses 112 creating a surface 114 co-planar with the surface 104 of the layer 100 of non-conducting diamond. The areas 114 and surface 104 provide the analysis surface in use.

The microelectrodes of the invention may be used in a wide variety of applications such as:
the measurement of trace heavy metals such as lead, cadmium, copper and zinc in the environment (e.g. Sono-Cathodic Stripping Voltammetry of Lead at a Polished Boron-Doped Diamond Electrode; Application to the Determination of Lead in River Sediment, Saterlay et al, Electroanalysis 1999, 11, No. 15, p 1083;
the detection of organic or bio-chemical compounds such as carboxylic acids in enology, food processing and wastewater analysis applications (see Chailapakul et al, Electrochem. Commun., 2000, Volume 2, p 422) or DNA in flow detection systems (Rao et al, New Diamond and Frontier Technology, vol. 13, No 2, 2003, p 79);
the detection of biomolecules such as thyroid hormones (Yvonne Naidoo, Electrichemical Behaviour of Boron Doped Diamond Electrodes, MSc Thesis, University of Pretoria, 2001).

The microelectrodes of the invention are suitable for use in sensors for monitoring one or more characteristics associated with fluids such as described in a co-pending patent application to Schlumberger Holdings Limited entitled: "System and method for sensing using diamond based microelectrodes", which is incorporated herein by reference.

The invention is further described with reference to the following non-limiting example.

EXAMPLE

A highly boron doped polycrystalline CVD diamond layer was grown to a thickness just above 500 μm and the substrate removed. Synthesis took place in a microwave plasma reactor using methods known in the art, at a pressure of $180 \times 10^3$ Pa, temperature of 1000° C. measured by pyrometry, and with a methane concentration of 2.5% and a diborane concentration of 15 ppm. The average specific electrical resistance of the layer was 0.75 ohm·meters.

The growth side of this wafer was then lapped and polished flat to a mirror finish and a thickness of approximately 0.5 mm, and 10×10 mm squares were lasered out using techniques well known to those skilled in the art. The nucleation side was fine lapped to remove the nucleation layer.

A 10×10 mm diamond plate was mounted on an X-Y table of a commercial 248 nm pulsed UV laser system (Exitech M5000). The optics train of the laser homogenised and projected the UV beam through a 20× reduction lens onto the polished surface of the diamond plate. A mask was placed in the beam just prior to the reduction lens and comprised of an AR coated fused silica plate partially coated with titanium. In the middle of the mask was a diamond shaped clear area of 20×10 mm with four 0.5 mm titanium coated circles positioned to form the primitive lattice of an hexagonal array.

Using a step and repeat action, the UV laser was used to ablate the diamond surface, with ablation masked in those areas defined by the titanium coated circles, to create an approximately hexagonal array of conical conducting CVD diamond pillars all over the diamond surface some 25 μm in diameter near their tops and 50 μm high with a nearest neighbour spacing of 250 μm. The laser was pulsed at 100 Hz at 300 mJ/pulse and 500 pulses needed for each etch position on the diamond plate.

The diamond plate was then removed from the UV laser system and cleaned chemically by boiling in sulphuric acid for five minutes. When cool, the sulphuric acid was decanted and the diamond plate washed in DI water and finally dried in an oven.

A ~100 μm layer of non-conducting CVD diamond was then grown over the array. This was done in a microwave plasma reactor using similar growth conditions, however with an absence of boron sources. The deposition temperature was estimated to be 950° C.

Additional growth experiments for both stages of growth determined that the invention can be realised using a wide range of growth conditions, the key features being to provide heavily boron doped diamond of high quality and good electrical conductivity in the first stage and diamond with no intentionally added boron and with a very high electrical resistance in the second layer. It is also in some instances advantageous to keep the grain size of the diamond layers, particularly the heavily boron doped layer, small compared to the electrode size. This is particularly useful where the precise properties of each electrode are critical since the boron concentration, which can vary in individual diamond crystallites due to the varying growth sectors, is then averaged out. Typically the grain size here (or more correctly the typical lateral dimensions of a growth sector) lay in the range of 3-10 µm compared to the 25-50 µm diameter of the doped electrodes.

Using techniques well known to those skilled in the art, the wafer was polished using conventional CVD diamond polishing technology to expose tops of the boron doped CVD diamond pillars, applying a careful final polishing step and creating an essentially planar surface with an approximately hexagonal array of electrically interconnected, 25 µm (nominal) discs of conducting diamond in a non-conducting diamond matrix.

Under an optical microscope, the polished array surface was flat and featureless apart from some random polishing digs and scratches and no height difference could be found between the conducting and non-conducting diamond areas when using Nomarski microscopy or a ZYGO NewView 5000 white light interferometer.

To show that an array had actually been created, the plate was electroplated with a commercial gold system (Aruna 311), which immediately showed a hexagonal gold pattern with the expected spacing on the top polished surface as the gold coated only the conducting discs of boron doped diamond exposed at the surface. On a sample not coated with gold, secondary electron channelling contrast in the SEM also showed the hexagonal array of conducting diamond sitting in the non-conducting diamond.

It was also found possible to delineate the surface features on the diamond array element by etching the diamond in an oxygen microwave plasma and then observing the surface with Nomarski microscopy. Under these conditions the heavily boron doped diamond pillars became lowered with respect to the bulk of the surface. SEM analysis of polished cross-sections of the array showed a sharp boundary between the underlying boron doped layer and the high purity overcoating, with the pillars of boron doped material breaking to the surface.

The invention claimed is:

1. A microelectrode comprising:
   a non-conducting layer formed from electrically non-conducting material presenting a planar surface;
   one or more projections of electrically conducting diamond extending at least partially through the non-conducting layer, the one or more projections presenting one or more planar areas of electrically conducting diamond;
   the one or more projections extend to the planar surface of the non-conducting layer presenting one or more planar areas of electrically conducting diamond co-planar with the planar surface of the electrically non-conducting material; and
   an electrical contact or contacts positioned directly on a back side of the one or more projections of electrically conducting diamond for connection to an external circuit,
   wherein the surface roughness of the one or more planar areas of the electrically conducting diamond is less than 15 nm.

2. A microelectrode according to claim 1, wherein the one or more projections of electrically conducting diamond present circular areas of electrically conducting diamond.

3. A microelectrode according to claim 1, wherein the one or more projections of electrically conducting diamond present elongate areas of electrically conducting diamond.

4. A microelectrode according to claim 1, wherein a plurality of projections of electrically conducting diamond are provided, each projection having a contact surface on its back side to provide individual connections between each of the projections and the external circuit.

5. A microelectrode according to claim 1, wherein the one or more projections extend to a rear surface of the non-conducting layer to provide the contact surface or surfaces for connection to the external circuit.

6. A microelectrode according to claim 1, wherein the one or more projections extend only part-way towards a rear surface of the non-conducting layer and holes are formed in the rear surface of the non-conducting layer to reveal the contact surface or surfaces on the back side of the one or more projections for connection to the external circuit.

7. A microelectrode according to claim 1, wherein the one or more projections extend to a rear surface of the non-conducting layer to provide the contact surface or surfaces for connection to the external circuit and an electrically conducting layer is provided on the rear surface of the non-conducting layer for providing an electrical connection to the one or more projections.

8. A microelectrode according to claim 1, wherein the electrically conducting diamond is boron doped diamond.

9. A microelectrode according to claim 1, wherein the one or more planar areas of electrically conducting diamond and co-planar surfaces are smooth.

10. A microelectrode according to claim 1, wherein the electrically conducting diamond is synthetic single crystal or polycrystalline diamond.

11. A microelectrode according to claim 1, wherein the non-conducting material is synthetic single crystal or polycrystalline diamond.

12. A microelectrode according to claim 1, wherein the one or more projections have one projection that has a width in a range 2 to 200 µm.

13. A microelectrode according to claim 1, wherein a plurality of projections of electrically conducting diamond are provided and a ratio of a separation between projections and a width of the projections exceeds 2.5, 5, or 10.

14. A microelectrode according to claim 1, wherein the one or more projections extend completely through the non-conducting layer.

15. A microelectrode according to claim 1, wherein a plurality of projections of electrically conducting diamond are provided, the projections providing two or more types for the electrode.

16. A microelectrode according to claim 15, wherein the two or more types are differentiated by one or more of: voltage applied; the use made of the voltage applied by the external circuit; concentration or type of dopant in the electrically conducting diamond; geometry or size of the types of the electrode.

17. A microelectrode comprising:
    a non-conducting layer formed from electrically non-conducting material presenting a planar surface;
    one or more projections of electrically conducting diamond extending at least partially through the non-conducting layer, the one or more projections presenting one or more planar areas of electrically conducting diamond;

the one or more projections extend to the planar surface of the non-conducting layer presenting one or more planar areas of electrically conducting diamond co-planar with the planar surface of the electrically non-conducting material; and an electrical contact or contacts positioned directly on a back side of the one or more projections of electrically conducting diamond for connection to an external circuit, wherein the one or more planar areas of electrically conducting diamond comprise polished surfaces having a surface roughness of less than 100 nm.

* * * * *